US010415078B2

(12) United States Patent
Seufferheld et al.

(10) Patent No.: US 10,415,078 B2
(45) Date of Patent: Sep. 17, 2019

(54) BACILLUS THURINGIENSIS TOXIN RESISTANCE ASSAY

(71) Applicant: The Board of Trustees of the University of Illinois, Urbana, IL (US)

(72) Inventors: Manfredo Jose Seufferheld, Cuidad Autonoma de Buenos Aires (AR); Chia-Ching Chu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 768 days.

(21) Appl. No.: 14/893,957

(22) PCT Filed: May 27, 2014

(86) PCT No.: PCT/US2014/039506
§ 371 (c)(1),
(2) Date: Nov. 25, 2015

(87) PCT Pub. No.: WO2014/193790
PCT Pub. Date: Dec. 4, 2014

(65) Prior Publication Data
US 2016/0115521 A1    Apr. 28, 2016

Related U.S. Application Data

(60) Provisional application No. 61/827,883, filed on May 28, 2013, provisional application No. 61/866,680, filed on Aug. 16, 2013.

(51) Int. Cl.
| | |
|---|---|
| *C12Q 1/37* | (2006.01) |
| *G01N 33/573* | (2006.01) |
| *C12Q 1/6888* | (2018.01) |
| *C12Q 1/689* | (2018.01) |

(52) U.S. Cl.
CPC .............. *C12Q 1/37* (2013.01); *C12Q 1/689* (2013.01); *C12Q 1/6888* (2013.01); *G01N 33/573* (2013.01); *C12Q 2600/158* (2013.01); *G01N 2333/32* (2013.01)

(58) Field of Classification Search
CPC ....... C12Q 1/37; C12Q 1/6888; G01N 33/573
See application file for complete search history.

(56) References Cited

PUBLICATIONS

Gassmann, AJ et al. Field-evolved resistance to Bt maize by western corn rootworm. PLoS One. 2011. 6(7): e22629. 7 pages. (Year: 2011).*
Engel, P et al. The gut microbiota of insects—diversity in structure and function. FEMS Microbiology Reviews. 2013. First published May 21, 2013. 37: 699-735. (Year: 2013).*
Hussein, HM et al. Beetle-specific Bacillus thuringiensis Cry3Aa toxin reduces larval growth and curbs reproduction in Spodoptera littoralis (Boisd.). Pest Managment Science. 2005. 61: 1186-1192. (Year: 2005).*
Chu et al. "Differential effects of RNAi treatments on field populations of the western corn rootworm" Pestic. Biochem. Physiol. 2014 110:1-6 Epub Feb. 27, 2014.
Curzi et al. "Abnormally high digestive enzyme activity and gene expression explain the contemporary evolution of a *Diabrotica* biotype able to feed on soybeans" Ecol Evol. 2012 2(8):2005-17 Epub Jul. 19, 2012.
Gassmann et al. "Field-evolved resistance to Bt maize by western corn rootworm" PLoS One. 2011;6(7):e22629 Epub Jul. 29, 2011.
Kaiser-Alexnat, R. "Protease activities in the midgut of Western corn rootworm (*Diabrotica virgifera virgifera LeConte*)" Journal of Invertebrate Pathology 2009 100:169-174.
Loseva et al. "Changes in protease activity and Cry3Aa toxin binding in the Colorado potato beetle: implications for insect resistance to *Bacillus thuringiensis* toxins" Insect Biochem Mol Biol. 2002 32(5):567-77.
Oppert et al. "*Bacillus thuringiensis* Cry3Aa protoxin intoxication of *Tenebrio molitor* induces widespread changes in the expression of serine peptidase transcripts" Comp Biochem Physiol Part D Genomics Proteomics. 2012 7(3):233-42 Epub May 2, 2012.
International Preliminary Report on Patentability in PCT/US2014/039506 dated Dec. 10, 2015.

* cited by examiner

*Primary Examiner* — Renee Claytor
*Assistant Examiner* — Susan E. Fernandez
(74) *Attorney, Agent, or Firm* — Licata & Tyrrell P.C.

(57) ABSTRACT

A method for monitoring resistance to a *Bacillus thuringiensis* pesticidal crystal protein is provided, which involves the measurement of protease activity or protease expression in the gut of adult insects.

3 Claims, 3 Drawing Sheets

Specification includes a Sequence Listing.

SEQUENCE LISTING

<160> NUMBER OF SEQ ID NOS: 20

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
ttgctgacat gacccaga                        19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
aatccagtag ggtgtgcca                                                19

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gccaatctag gtgccttcga                                               20

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
tggaaactgg acctacgct                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
atccacatgg actgcagga                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
cggatagcat gacctccca                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
agtccaccaa caatgggct                                                19

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide -continued

```
<400> SEQUENCE: 8
cacatactgc aattgggcca                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
agtacgactg gaacagtgga                                                    20

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
gggtatgtag cgtcagtgg                                                     19

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ctacacattt gctagcccca                                                    20

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
ccagtttact ccccaggag                                                     19

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
atgcatagca tcccaggga                                                     19

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
tagacttgag caggtgcag                                                     19

<210> SEQ ID NO 15
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
aacgccatgg tctctcttcc gaat                                              24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
tggaaactgg acctacgcta gcaa                                              24

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
ggatggcaaa tcgaacgtaa a                                                 21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
gggaaggata gcatccaaag c                                                 21

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
tggactcgac tgaaccagca taca                                              24

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 20
atgttgtctc cgtgccatcc tgaa                                              24
```

BACILLUS THURINGIENSIS TOXIN RESISTANCE ASSAY

This application is a U.S. National Stage Application of PCT/US2014/039506 filed May 27, 2014 and claims benefit of priority to U.S. Provisional Patent Application Ser. Nos. 61/866,680, filed Aug. 16, 2013, and 61/827,883, filed May 28, 2013, the contents of which are incorporated herein by reference in their entireties.

This invention was made with government support under contract number 2009-35505-06012 awarded by the United States Department of Agriculture. The government has certain rights in the invention.

INTRODUCTION

Background

Western Corn Rootworm (WCR; *Diabrotica virgifera virgifera* LeConte)) is one of the most important insect pests of corn in the United States and Canada, with losses estimated at more than $1 billion annually. Until the mid-1990s, annual crop rotation between corn and soybeans was an effective pest management strategy and virtually eliminated the need for corn rootworm-targeted chemical control. However, broad adoption of crop rotation decreased landscape heterogeneity and selected for behavioral resistance to crop rotation, leading to a costly escalation of insecticide use to protect the formerly "rootworm-free" rotated corn. The impact of rotation resistance continues to spread as the range of the rotation resistant WCR expands and more growers face uncertainty about the presence of rotation resistant WCR in their corn and soybean fields.

Rotation resistant WCR was the incentive behind the development of genetically modified corn varieties that express pesticidal crystal proteins derived from the soil bacterium *Bacillus thuringiensis* (Bt), commonly referred to as "Cry proteins" or "Cry peptides." These proteins are globular proteins, which accumulate as protoxins in crystalline form during the sporulation stage of *B. thuringiensis*. Within the pest digestive tracts, the crystals are solubilized to release protoxins in the midgut of the pest. The protoxins are converted into toxic fragments through digestion by gut proteases. In general, the toxicities of these Cry proteins are specific to their target insect species, but relatively harmless to non-targeted organisms.

A large portion of corn planted in the U.S. is Bt corn (i.e., corn that recombinantly expresses one or more Cry proteins or peptides), with the Cry3bb1 toxin being the major toxin deployed against rootworms. However, corn rootworm resistance to Bt corn has been documented (Gassmann, et al. (2011) *PLoS ONE* 6:e22629). Moreover, suspected Bt resistant populations of WCR have been found in northern Illinois and Michigan. Given that this trend is spreading, and that problem fields have appeared with considerable geographic separation, the development of Bt resistance is a growing concern. Indeed, Bt resistance could be disastrous for growers who rely on Bt technology for WCR management. Therefore, there is a need for improvements in resistance management and a more integrated approach to the use of Bt crops in order to stop and/or delay the evolution of resistance.

A neonate larvae-based bioassay, i.e., a seedling-based assay (Gassmann, et al. (2011) supra), has been described. While this test is accurate, it has several limitations. First, this assay requires numerous steps and a large amount of infrastructure including a greenhouse. Furthermore, this test can only be used with first instar larvae, which are very laborious to obtain and maintain. Moreover, the assay takes several months to complete due to the biology of the insect, which requires a long period of cold exposure (approximately three months) for the laid eggs to develop a viable larva. In addition, this test is based on percentage of dead larvae, and therefore may miss developing resistance in the field tested.

If resistant rootworms are few and far between, crop damage may be minimal. Problems arise when a population is mostly composed of resistant insects. Thus, it is critical to have a fast and accurate method for monitoring evolution of resistance as it happens, so that strategies for genetically modified crop management can be adjusted or changed. The present invention meets this need in the art.

SUMMARY OF THE INVENTION

The present invention is a method of monitoring for resistance to a *Bacillus thuringiensis* pesticidal crystal protein by (a) collecting adult Coleopteran insects from a field of plants; (b) feeding the adult Coleopteran insects a *Bacillus thuringiensis* pesticidal crystal protein (Bt) diet and a non-Bt diet; (c) obtaining gut samples from the adult Coleopteran insects fed the Bt diet and non-Bt diet; (d) measuring a level of protease activity or expression in the gut samples from the adult Coleopteran insects fed the Bt diet and non-Bt diet; and (e) determining resistance or susceptibility to the Bt pesticidal crystal protein based upon the level of protease activity or expression in the gut samples from the adult Coleopteran insects fed the Bt diet and non-Bt diet. In one embodiment, the Coleopteran is a *Diabrotica virgifera, D. barberi*, or *D. undecimpunctata howardi*. In a further embodiment, the field of plants is corn, e.g., corn that expresses a *Bacillus thuringiensis* pesticidal crystal protein.

In one embodiment, the step of determining resistance or susceptibility to the Bt pesticidal crystal protein includes (i) averaging the level of protease activity or expression in the gut samples from the adult Coleopteran insects fed the Bt diet; (ii) averaging the level of protease activity or expression in the gut samples from the adult Coleopteran insects fed non-Bt diet; and (iii) comparing the average level of protease activity or expression in the gut samples from the adult Coleopteran insects fed the Bt diet and non-Bt diet, wherein resistance to the pesticidal crystal protein is indicated if higher protease activity or expression is measured in the adult Coleopteran insects fed the Bt diet as compared to the adult Coleopteran insects fed the non-Bt diet.

In an alternative embodiment, the step of determining resistance or susceptibility to the Bt pesticidal crystal protein involves (i) averaging the level of protease activity or expression in the gut samples from the adult Coleopteran insects fed the Bt diet; (ii) averaging the level of protease activity or expression in the gut samples from the adult Coleopteran insects fed non-Bt diet; (iii) calculating a ratio of the average level of protease activity or expression in the gut samples from the adult Coleopteran insects fed the Bt diet to the average level of protease activity or expression in the gut samples from the adult Coleopteran insects fed non-Bt diet to obtain a retained level of protease activity or expression; and (iv) comparing the retained level (e.g., calculated ratio) of protease activity or expression with a threshold protease activity or expression standard ratio, wherein resistance to the pesticidal crystal protein is indicated if the retained level of protease activity or expression exceeds the threshold protease activity or expression standard ratio. In accordance with this embodiment, the threshold protease activity or expression standard can be the mean of an average retained level of protease activity or expression of resistant populations of adult Coleopteran insects, and an average retained protease activity of susceptible populations of adult Coleopteran insects, or the retained activity or expression level (ratio) of a Coleopteran insect population that is in the process of developing resistance to the toxin.

BRIEF DESCRIPTION OF THE DRAWINGS

FIG. 1 shows the effect of Bt corn diets on general gut cysteine protease activities of WCR adults. Different letters indicate statistically significant differences (P<0.05) across groups. Adult WCRs from two field populations, Paxton, Ill. (PIL) and Urbana, Ill. (UIL), were collected from Bt and non-Bt corn fields, respectively, and sampled for their gut protease activity. Additional insects from the two populations were experimentally kept on either non-Bt corn or Bt corn diets under laboratory conditions and gut samples were collected to measure protease activity. Constitutive cysteine protease activities of WCRs under these treatments were measured and expressed in the units of absorbance change (due to p-nitroaniline released from substrate hydrolysis) per minute with extractions from 1 mg gut tissue.

FIG. 2 shows a model for resistance detection. Values in the y-axis indicate ratios of averaged cysteine protease activity of each tested Coleopteran population fed on Bt or non-Bt plant tissue, while the different populations are listed in the x-axis. The filled bar represents the ratio value of a Coleopteran population that is determined to be a population whose resistance level to Bt lies between resistant and susceptible populations thereby acting as a threshold. Populations whose ratio values exceed the threshold (see first two bars) are considered resistant (Resist.) or suspected resistant (Suspect.), while populations whose ratio is below the threshold (see last two bars) are considered susceptible (Suscept.).

FIGS. 3A and 3B show the expression of different cathepsin B genes in the guts of adults WCR fed on either Sweet Corn (SC) or BT-corn (expressing Cry3Bb1) for 5 days. Bars: Standard Error. Filled bars, Champaign population; open bars, Paxton population (suspected Bt-resistant population). Different letters indicate statistically significant differences (P<0.05) between corn genotypes for each population. Asterisks (*) indicate significant differences (P<0.05) between populations for each corn genotype.

FIGS. 4A-4C show the expression of different Cathepsin L genes in the guts of adults WCR fed on either Sweet Corn (SC) or BT-corn for 5 days. Bars: Standard Error. Filled bars, Champaign population; open bars, Paxton population (suspected Bt-resistant population). Different letters indicate statistically significant differences (P<0.05) between corn genotypes for each population. Asterisks (*) indicate significant differences (P<0.05) between populations for each corn genotype.

DETAILED DESCRIPTION OF THE INVENTION

Bt toxins have been shown to be most effective in killing corn rootworm at the first instar larvae stage. After that it has been suggested that larvae became more resistant or immune to Bt toxins and adults are relatively unaffected by it. Therefore, conventional assays have been developed using a larvae-based read-out. It has now been found that exposure of corn rootworm adults to Bt toxin changes the physiology of the gut, as determined by measurable changes in proteolytic activity. Accordingly, the present invention provides a method for monitoring the development of Bt resistance in corn rootworm field populations by measuring these biochemical and/or molecular responses in adult insect guts. The method of this invention is a significant advancement in monitoring Bt resistance since it does not require handling larvae, does not require costly facilities and can be carried out in less than two weeks. Moreover, the sensitivity of the bioassay of this invention is high because the assay does not test survival, rather proteolytic activity (gut physiology) is determined, which can discriminate between a resistant population and a population that is at risk of developing resistance even before visual damage is evident in the field. Furthermore, the assay of the invention can determine whether an insect is developing resistance to other Cry toxins in single or in pyramided products. This provides a significant monitoring tool for Insect Resistance Management (IRM) and product development, e.g., transgenic or classical breeding strategies.

As indicated, this invention provides, in part, assays for monitoring the development of resistance to crystal protein insect toxins (Cry proteins), such as Cry proteins from *Bacillus thuringiensis* (Bt), e.g., Cry1A, Cry1, Cry3, Cry5, Cry8, Cry9, etc. (also commonly referred to as Bt toxins), by measuring proteolytic enzyme activity or protease expression (protein or gene) in the gut of an adult insect. These assays can be practiced in the form of simple kits to screen for the presence or absence of resistant insects. In some embodiments, levels of protease activity or protease expression in the adult gut are assessed in insects fed a Bt and non-Bt diet to compare the absolute or relative levels of protease activity or expression in response to each diet.

As used herein, the terms "Bt crop" or "Bt diet" are intended to mean plants that have been genetically engineered to express one or more Cry proteins. By comparison, a "non-Bt crop" or "non-Bt diet" is used herein to refer to plants that have not been genetically engineered to express one or more Cry proteins. In particular embodiments of this invention, the method is used to monitor resistance to Cry proteins expressed by transgenic corn. In this respect, particular embodiments of the invention embrace a Bt corn crop. As used herein, the term "corn" means *Zea mays* or maize and includes all plant varieties that can be bred with corn, including wild maize species. In one embodiment, the disclosed methods are useful for managing resistance in a plot of pest resistant corn, where corn is systematically followed by corn (i.e., continuous corn). In another embodiment, the methods are useful for managing resistance in a plot of first-year pest resistant corn, that is, where corn is followed by another crop (e.g., soybeans), in a two-year rotation cycle. Other rotation cycles are also contemplated in the context of the invention, for example where corn is followed by multiple years of one or more other crops, so as to prevent resistance in other extended diapause pests that may develop over time.

It has been previously shown that ingestion of Bt toxin has no adverse effect on adult insect (WCR) longevity (Nowatzki, et al. (2006) *J. Econ. Entomol.* 99:927-930). However, it has been shown that feeding of Bt corn tissues could reduce the fecundity of WCR adults (Meissle, et al. (2011) *Pest Management Sci.* 67:807-814). The present finding that Bt susceptibility/resistance could be correlated with significant changes in the resilience of gut function (i.e., proteolysis) to attack by Bt toxin is thus concordant with the observed detrimental effects of Bt corn on WCR adult fecundity. In particular, it was observed that the activity of cysteine protease activity was altered in response to Bt. More specifically, it was found that Bt significantly suppressed protease activity in the gut of insects susceptible to Bt, whereas high protease activity was retained in the gut of insects that were suspected to be resistant to Bt (i.e., high root damage in Cry3Bb1 Bt-corn fields (>1.0 NIS), or high adult density in Bt-corn fields). Therefore, this invention stems, in part, from the observation that changes in protease activity and/or expression of relevant genes in the susceptible adult gut are evident upon consumption of Bt corn.

This invention finds use in monitoring susceptibility/resistance in a variety of insects that are known to be susceptible to Bt toxin including insects from the orders Lepidoptera, Diptera, and Coleoptera. In certain embodiments, the insects being monitored are of the order Coleoptera including weevils from the families Anthribidae, Bruchidae, and Curculionidae, including, but not limited to, *Anthonomus grandis* Boheman (boll weevil), *Lissorhoptrus oryzophilus* Kuschel (rice water weevil), *Sitophilus granarins* Linnaeus (granary weevil), *S. oryzae* Linnaeus (rice weevil), *Hypera punctata* Fabricius (clover leaf weevil), *Cylindrocopturus adspersus* LeConte (sunflower stem weevil), *Smicronyx fulvus* LeConte (red sunflower seed weevil), *S. sordidus* LeConte (gray sunflower seed weevil), *Sphenophorus maidis* Chittenden (maize billbug); and flea beetles, cucumber beetles, rootworms, leaf beetles, potato beetles, and leafminers in the family Chrysomelidae including, but not limited to, *Leptinotarsa decemlineata* Say (Colorado potato beetle), *Diabrotica virgifera virgifera* LeConte (western corn rootworm), *D. barberi* Smith & Lawrence (northern corn rootworm), *D. undecimpunctata howardi* Barber (southern corn rootworm), *Chaetocnema pulicaria* Melsheimer (corn flea beetle), *Phyllotreta cruciferae* Goeze (corn flea beetle), *Colaspis brunnea* Fabricius (grape colaspis), *Oulema melanopus* Linnaeus (cereal leaf beetle), and *Zygogramma exclamationis* Fabricius (sunflower beetle). Also included are beetles from the family Coccinellidae including, but not limited to, *Epilachna varivestis* Mulsant (Mexican bean beetle); chafers and other beetles from the family Scarabaeidae including, but not limited to, *Popillia japonica* Newman (Japanese beetle), *Cyclocephala borealis* Arrow (northern masked chafer, white grub), *C. immaculata* Olivier (southern masked chafer, white grub), *Rhizotrogus majalis* Razoumowsky (European chafer), *Phyllophaga crinita* Burmeister (white grub), *Ligyrus gibbosus* De Geer (carrot beetle); carpet beetles from the family Dermestidae; wireworms from the family Elateridae; bark beetles from the family Scolytidae and beetles from the family Tenebrionidae. In some embodiments, the methods of the invention are of use in monitoring adults from the genus *Diabrotica*. In other embodiments, the methods of the invention are of use in monitoring adult corn rootworms. In particular embodiments, the methods of the invention are of use in monitoring *Diabrotica virgifera virgifera* LeConte (western corn rootworm) adults.

In other embodiments, the insects being monitored are of the order Lepidoptera including, but not limited to, *Ostrinia nubilalis* (european corn borer), *Diatraea saccharilis* (sugarcane borer), *Agrotis ipsilon* (Black Cutworm), *Helicoverpa zea* (corn Earworm), *Spodoptera frugiperda* (fall armyworm), *Anthonomus grandis* (cotton ball weevil), *Bombyx mori* and *Manduca sexta* (silkworms). In some embodiments, the methods of the invention are of use in monitoring adult sugarcane borer or fall armyworms.

As is known in the art, the western corn rootworm (WCR; *D. virgifera virgifera*), northern corn rootworm (NCR; *D. barberi*), and southern corn rootworm (SCR; *D. undecimpunctata howardi*) share a similar lifecycle, which includes four stages: the egg, larva, pupa, and adult. Every year during late spring the rootworm larvae hatch and begin their univoltine life cycle. The larvae are attracted to corn roots by the $CO_2$ emitted from the root tips and begin to feed on the root tissues. The corn rootworm larvae go through three instars that each lasts seven to ten days. After completing the three developmental stages (instars), the rootworm larvae will pupate in the soil. During this dormant pupal stage, the larvae will develop into adult beetles. The WCR and NCR adults (beetles) emerge from the soil in the summer and may feed on corn foliage, pollen, silk or kernels. The female rootworm beetles are usually mated soon after emergence. They then feed on corn plants for approximately two weeks, and then return to the soil to lay eggs. The beetles will eventually die in the soil after laying all of the eggs. Therefore, in accordance with this invention, the adult insect used in the methods described herein refers to the adult beetle that emerges from the soil.

According to the methods of this invention, protease activity and/or protease expression (i.e., protein or nucleic acids) are measured in the gut of the adult insect. In particular embodiments, the activity or expression of cysteine proteases is measured. Cysteine proteases that can be measured in accordance with this invention include, but are not limited to cathepsin proteases (e.g., cathepsin L, cathepsin B, and cathepsin H) and papain. In addition to cysteine proteases, the level or activity of other proteases can also be determined including, but not limited to, aspartic proteases such as pepsin; metalloproteases such as saccharolysin; aminopeptidases; and serine proteases such as trypsin, chymotrypsin, elastase, plasmin, and thrombin, or other digestive enzymes such as cellulases or amylases.

The activity of proteases of this invention can be detected using any conventional reagent and/or technique. Such protease assays generally include a peptide substrate attached to one or more detectable labels, e.g., fluorophores or chromophores, which are released when the peptides substrate is cleaved. Typical cathepsin substrates include, e.g., Phe-Arg, Arg-Arg, and Glu-Phe-Leu as well as casein. Other suitable protease cleavage sequences are known in the art and a comprehensive list of proteases and their cognate cleavage sequences is available from the MEROPS database located on the world-wide web (see Rawlings, et al. (2002) *Nucl. Acids Res.* 30:343-346). The substrates can be covalently linked to labels such as p-nitroaniline, BODIPY dyes, 7-amino-4-methylcoumarin (AMC), 7-amino-4-trifluoromethylcoumarin (AFC), 7-Amino-4-chloromethylcoumarin (CMAC), rhodamine 110, and the like. Moreover, the protease substrate can be flanked by reporter proteins suitable for fluorescence resonance energy transfer (FRET).

Protease activity can be detected in a tube- or plate-based assay using the above-referenced labeled substrates, or alternatively protease activity can be assessed using zymographic analysis. Zymography is a type of gel electrophoresis that uses a polyacrylamide gel co-polymerized with a substrate in order to detect enzyme activity. Cathepsin zymography separates different cathepsins and has been used to detect femtomole quantities of mature cathepsin K (Li, et al. (2010) *Anal. Biochem.* 401:91-8).

Similarly, protein expression can be determined by routine methods including, but not limited to, western blot analysis, dot blot analysis, ELISA and the like. Such assays are typically referred to as immunoassays, which use antibodies, or fragments thereof, having the desired specificity for one or more proteases. Numerous protocols for competitive binding (e.g., ELISA), latex agglutination assays, immunoradiometric assays, and kinetics (e.g., BIACORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. Such assays can also be used in measuring the amount or level of one or more proteases in the gut of an adult insect.

In an alternate embodiment, the amount or level of the protease is detected via the presence of nucleic acid sequences encoding the protease (e.g., messenger RNA (mRNA)). Nucleic acids encoding a protease can be detected using any well-known method including, but not limited to, northern blot analysis, reverse-transcriptase PCR, PCR, microarray, next-generation sequencing and the like. Due to the ease of use, it is generally desirable to detect the nucleic acid sequences using a PCR-based approach. In general, this involves contacting the sample with two or more PCR primers which specifically hybridize with nucleic acids encoding a protease of interest or which flank the coding region of protease of interest, subjecting the sample to multiple steps of PCR amplification and detecting the presence or absence of the amplified sequence (e.g., using gel analysis, blotting methods, or fluorescently-labeled primers). Alternatively, an oligonucleotide, a cDNA, an antibody, or a fragment thereof, which interacts with at least a portion of the nucleic acid encoding a protease of interest is configured in an array on a chip or wafer and used for measuring nucleic acids encoding a protease of interest. Briefly, these techniques involve methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251(4995):767-73).

Primers or oligonucleotides for use in this embodiment can be selected from any region of the locus encoding a protease described herein and generally specifically anneal and amplify at least a portion of a nucleic acid encoding a protease and no other nucleic acid encoding a closely related protein. In general, suitable primers are 12 to 30 bp in length and generate a PCR amplicon suitable for gene expression analysis, e.g., 50, 100, 200 400, 600, 1000 bp or more in length. The fundamentals of quantitative or semi-quantitative reverse transcriptase PCR (qRT-PCR, qPCR, real-time PCR or semi-quantitative RT-PCR) are well-known to the skilled artisan. See, e.g. McPherson, et al., PCR, A Practical Approach, IRL Press, Oxford, Eng. (1991); Breljak, et al. (2005) *Food Technol. Biotechnol.* 43:379-388; Gottwald, et al. (2001) *Electrophoresis* 22:4016-22. By way of illustration, exemplary gene names, accession numbers, and primer sequences for WCR cathepsin-like protease transcripts are provided in Table 1.

TABLE 1

| Gene Name | Accession No. | Primer | Sequence | SEQ ID NO: |
|---|---|---|---|---|
| DvCAL1 | AF190653 | Forward | TTGCTGACATGACCCCAGA[1] | 1 |
|  |  | Reverse | AATCCAGTAGGGTGTGCCA[1] | 2 |
| DVRS5 | AJ583508 | Forward | GCCAATCTAGGTGCCTTCGA[1] | 3 |
|  |  | Reverse | TGGAAACTGGACCTACGCT[1] | 4 |
| DvRS6 | AJ583509 | Forward | ATCCACATGGACTGCAGGA[1] | 5 |
|  |  | Reverse | CGGATAGCATGACCTCCCA[1] | 6 |
| DvRS29 | AJ583510 | Forward | AGTCCACCAACAATGGGCT[1] | 7 |
|  |  | Reverse | CACATACTGCAATTGGGCCA[1] | 8 |
| DvRS30 | AJ583511 | Forward | AGTACGACTGGAACAGTGGA[1] | 9 |
|  |  | Reverse | GGGTATGTAGCGTCAGTGG[1] | 10 |
| DvRS33 | AJ583512 | Forward | CTACACATTTGCTAGCCCCA[1] | 11 |
|  |  | Reverse | CCAGTTTACTCCCCAGGAG[1] | 12 |
| DvRS40 | AJ583513 | Forward | ATGCATAGCATCCCAGGGA[1] | 13 |
|  |  | Reverse | TAGACTTGAGCAGGTGCAG[1] | 14 |
| DVRS5 | AJ583508 | Forward | AACGCCATGGTCTCTCTTCC GAAT[2] | 15 |
|  |  | Reverse | TGGAAACTGGACCTACGCTA GCAA[2] | 16 |

[1]Primers of use in semi-quantitative RT-PCR.
[2]Primers of use in qPCR.

Typically, the method of this invention will include a positive and/or negative control to assess the accuracy of the method. Also, internal reference genes can be used for comparing relative expression levels of target genes. In this regard, housekeeping genes such as EF-1α can be used as an internal control. EF-1α primers suitable for semi-quantitative RT-PCR include forward primer GGATGGCAAATC-GAACGTAAA (SEQ ID NO:17) and reverse primer GGGAAGGATAGCATCCAAAGC (SEQ ID NO:18). Exemplary EF-1α primers for qRT-PCR include forward primer TGGACTCGACTGAACCAGCATACA (SEQ ID NO:19) and reverse primer ATGTTGTCTCCGTGCCATC-CTGAA (SEQ ID NO:20).

The results presented herein indicate that Bt consumption exerts a negative influence on gut cysteine protease activity and/or expression, and that resistant and susceptible insects fed a Bt crop and a non-Bt crop respond differently to Bt. In particular, whereas an insect that is susceptible to Bt will exhibit a significant decrease in protease activity and expression in response to a Bt crop as compared to a non-Bt crop, an insect that is resistant to Bt will exhibit an increase in protease activity and expression in response to a Bt crop as compared to a non-Bt crop.

The present invention is a method for monitoring for resistance or susceptibility to a Bt pesticidal crystal protein by collecting adult Coleopteran insects from a field; feeding a first group of the adult Coleopteran insects a Bt diet and feeding a second group of the adult Coleopteran insects a non-Bt diet; obtaining gut samples from the first and second groups of adult Coleopteran insects respectively fed the Bt diet and non-Bt diet; measuring a level of protease activity in the gut samples from the first and second groups of adult Coleopteran insects respectively fed the Bt diet and non-Bt diet; and determining resistance or susceptibility to the Bt pesticidal crystal protein based upon the level of protease activity in the gut samples from the first and second groups of adult Coleopteran insects fed the Bt diet and non-Bt diet, respectively. Levels of protease activity in the gut samples can be from a single measurement or can be the average of two or more measurements from the gut samples. In one embodiment, the adult Coleopteran insects are collected from a field of a Bt crop. In another embodiment, the adult Coleopteran insects are collected from a field of a Bt crop and subsequently fed a Bt diet that expresses the same Cry protein. In an alternative embodiment, the adult Coleopteran insects are collected from a field of a Bt crop and subsequently fed a Bt diet that expresses one or more different Cry proteins.

The present invention is also a method for monitoring for resistance or susceptibility to a Bt pesticidal crystal protein by collecting adult Coleopteran insects from a field; feeding a first group of the adult Coleopteran insects a Bt diet and feeding a second group of the adult Coleopteran insects a non-Bt diet; obtaining gut samples from the first and second groups of adult Coleopteran insects fed the Bt diet and non-Bt diet, respectively; measuring a level of protease expression in the gut samples from the first and second groups of adult Coleopteran insects fed the Bt diet and non-Bt diet, respectively; and determining resistance or susceptibility to the Bt pesticidal crystal protein based upon the level of protease expression in the gut samples from the first and second groups of adult Coleopteran insects fed the Bt diet and non-Bt diet, respectively. Levels of protease expression in the gut samples can be from a single measurement or can be the average of two or more measurements. In one embodiment, the adult Coleopteran insects are collected from a field of a Bt crop. In another embodiment, the adult Coleopteran insects are collected from a field of a Bt crop and subsequently fed a Bt diet that expresses the same Cry protein. In an alternative embodiment, the adult Coleopteran insects are collected from a field of a Bt crop and subsequently fed a Bt diet that expresses one or more different Cry proteins.

In one embodiment of the methods of this invention, susceptibility to a pesticidal crystal protein is indicated if lower protease activity/expression is measured in adult Coleopteran insects fed the Bt diet as compared to adult Coleopteran insects fed the non-Bt diet. In certain embodiments, the level of protease activity/expression is compared with the level of protease activity/expression in one or more controls, e.g., a Bt resistance and/or Bt susceptible population of insects.

In another embodiment, resistance or susceptibility to a pesticidal crystal protein is determined by calculating a ratio (i.e., dividing) of the measured protease activity/expression of adult Coleopteran insects fed the Bt diet to the measured protease activity/expression of adult Coleopteran insects fed non-Bt diets to obtain a retained protease activity/expression value, e.g., a percentage, wherein susceptibility is indicated if the retained protease activity/expression is lower than a threshold protease activity/expression standard. In accordance with this embodiment, the threshold protease activity/expression standard can be an amount of retained protease activity/expression determined from populations of adult Coleopteran insects, which have been confirmed by one or more assays, e.g., a seedling-based assay (Gassmann, et al. (2011) supra), to be resistant (or suspected resistant) or susceptible. For example, as illustrated in FIG. 2, whereas confirmed resistant or suspected resistant populations may retain between 35% and 50% protease activity when fed a Bt diet as compared to a non-Bt diet, confirmed susceptible populations may retain between 10% and 12% protease activity when fed a Bt diet as compared to a non-Bt diet. As such, a threshold protease activity standard for determining resistance or susceptibility would be an average of the retained protease activity of the resistant/suspected resistant and susceptible populations, e.g., approximately 27%. Using this comparative analysis, the threshold protease activity/expression standard can be determined using Equation 1.

$$\text{(Average Retained Protease Activity/Expression of Resistant/Suspected Resistant Populations)} + \text{(Average Retained Protease Activity of Susceptible Populations)} \div 2 = \text{Threshold Protease Activity/Expression Standard} \qquad \text{(Equation 1)}$$

In certain embodiments of Equation 1, Average Retained Protease Activity/Expression of Resistant Populations is averaged with Average Retained Protease Activity/Expression of Susceptible Populations. In addition, a suitable threshold can be the retained activity or expression level (ratio) of a Coleopteran insect population that is in the progress of developing resistance to the toxin.

In another embodiment, resistance or susceptibility to a pesticidal crystal protein is determined using absolute protease activity and/or expression levels. By way of illustration, whereas total retained protease activity in the gut of susceptible adult Coleopteran insects may be in the range of 1 to 15 nmol/g min, total retained cathepsin protease activity in the gut of resistant adult Coleopteran insects may be in the range 20 to 40 nmol/g min. In this respect, a Threshold Protease Activity Standard may be set at between 16 and 19 nmol/g min, wherein retained protease activity levels above 19 nmol/g min indicate a resistant population and retained protease activity levels below 16 nmol/g min indicate a susceptible population. Protease levels for setting the Threshold Protease Activity Standard can be based on levels determined in a particular county, state or region and therefore Threshold Protease Activity Standards may vary for different counties, states or regions.

Moreover, it is contemplated that the methods of this invention can be carried out for more than one protease. In this respect, the activity or expression of a combination of two, three or more proteases can be determined and relative activity ratio of the proteases to each other can be used to assess resistance or susceptibility to Bt.

In conjunction with the method of this invention is a kit for monitoring for resistance to Bt. A kit of the invention includes a container containing at least one agent of use in measuring protease activity (e.g., a labeled substrate). Alternatively, the kit contains an antibody or suitable primers (e.g., those disclosed herein) for measuring protease expression. The kit can further contain Bt-resistant and/or -susceptible insects or gut extracts as controls. In one embodiment, the kit includes one or more isolated proteases for use in the generation of a standard curve. For example, the kit can include papain and/or cathepsin B with known specific activity. Moreover, the kit can also contain other solutions necessary or convenient for carrying out the invention. The container can be made of glass, plastic or foil and can be a vial, bottle, pouch, tube, bag, etc. The kit may also contain written information, such as procedures for carrying out the method of the invention or analytical information, such as the amount of reagent contained in the first container means. The container can be in another container, e.g., a box or a bag, along with the written information.

Using the methods of this invention, it will be possible to generate real-time resistance status maps and models that include agro-ecological and managements factors to predict the evolution of resistance at the county, state or national levels. Moreover, the principles used in the described methods may be applied to the detection of sensitivity of an organism to toxins targeting the gut. Accordingly, as an additional step of the methods of this invention, the management of one or more crops can be modified or adjusted to account for the presence or emergence of resistance to the Bt pesticidal crystal protein. For example, crop rotation practices can be initiated or altered (e.g., by increasing the number of years before the next corn crop is planted) to reduce to impact of the resistant insects.

The invention is described in greater detail by the following non-limiting examples.

EXAMPLE 1

Protease Activity in WCR Adults

It was observed that Bt toxins affected the gut physiology of WCR adults. These results are supported by an extensive study of populations of WCR throughout Illinois for three years. It was found that Bt toxins affected the cysteine protease activity of the guts of WCR adults. Initially, the activity of two populations of WCR from Paxton and Champaign were measured.

The Paxton, Ill. population came from a stacked pyramid Bt corn (which includes Cry3Bb1 and Cry34/35) that had been used in that field for at least 5 to 6 consecutive years. This field had a high abundance of adults in the field, and thus, had the potential for having a resistant population.

Figure 1:
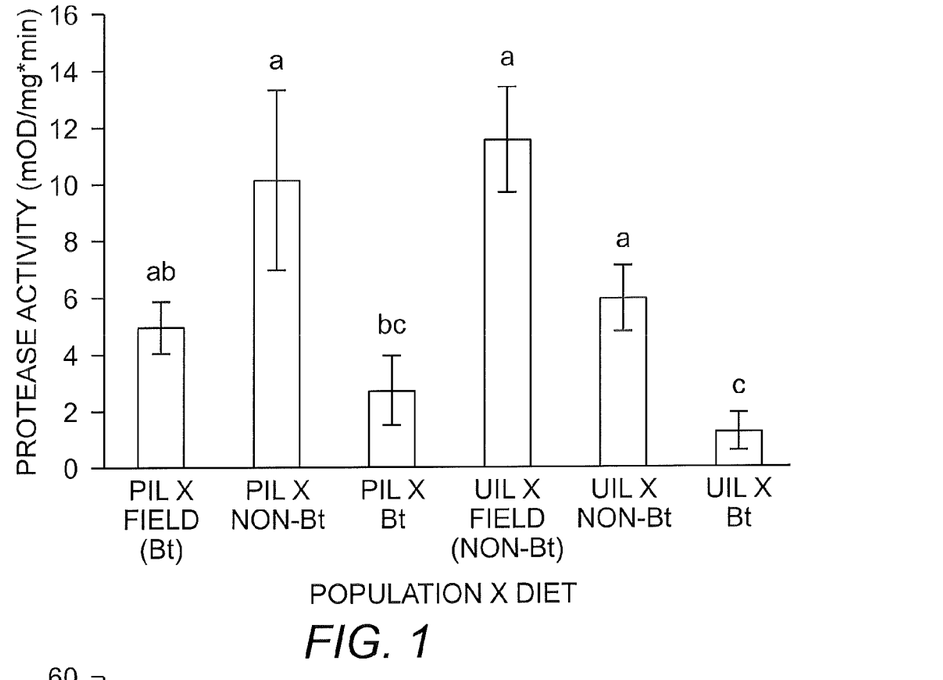

The Urbana, Ill. (L40) population was a population from a rotated non-Bt corn plot. As shown in FIG. 1, Bt corn significantly reduced the activity of cysteine proteases in both populations. This effect was reverted by feeding WCR adults with non-Bt corn diets. The recovery of the activity was reverted again once the insects were re-exposed to Bt-corn.

These data indicate that the ingestion of corn tissues expressing Bt toxin has a negative impact on gut proteolytic activity in adults. Furthermore, these data indicate that gut physiology may serve as an indicator for measuring susceptibility of WCR to attack by Bt toxins; in other words, the degree that WCR biology is impacted by the toxin. While this could be considered counter-intuitive, it is postulated that the assay identifies insects having gut systems that are resilient to attack by the toxins, because gut physiology is nutritionally crucial for insect fitness. In this regard, adult insects are good targets for monitoring any physiological/genetic adaptation of WCR larvae to Bt toxins because of their ease of handling and detectable response to the assay without mortality.

Based on the above results, additional experiments were conducted with three populations of insects that originated from fields where WCR were suspected to be resistant to Bt Cry3Bb1, two from Illinois (Ionia and Sangamon populations) and one population from Michigan (Mercer population). For comparison, two susceptible populations, a population from Champaign-Urbana, Ill. (Urbana population) and a laboratory-reared population that had never been exposed to Bt toxins (BND population), were included in the analysis. Susceptible (BND and Urbana) and suspected Bt-resistant WCR populations (collected from Bt corn fields with abnormally high root damage) were fed a non-Bt or Bt (Cry3Bb1) corn diet and gut cysteine protease activity was determined. The results of this experiment indicated that gut proteolytic activity of WCR adults was affected by Bt toxins (Table 2). However, the reduction in cysteine protease activity in insects that had not been exposed to Bt vs. insects that were fed a Bt diet was only statistically significant in the susceptible populations (i.e., BND and Urbana; after square-root transformation), but not in populations that were collected from Bt-corn fields exhibiting high root damages (NIS>1.0), or abnormally high adult density.

TABLE 2

| Population | Gut Cysteine Protease Activity (mOD/mg gut*minute) | | Significant decrease[a,b] |
|---|---|---|---|
| | Non-Bt Diet | Bt Diet | |
| BND | 6.100 | 1.804 | ** |
| Urbana | 0.345 | 0.139 | * |
| Mercer | 0.380 | 0.11 | |
| Ionia | 1.091 | 0.399 | |
| McDonough | 1.841 | 1.127 | |
| Sangamon | 0.205 | 1.030[c] | |

BND: Non-diapause WCR colony.
[a]Significantly lower protease activities on Bt diets (one-tailed test) are indicated by asterisks: * P < 0.05, ** P < 0.01.
[b]Data were square-root transformed for statistical analysis.
[c]Significantly higher protease activity (P < 0.05) on Bt diet was detected.

Figure 2:
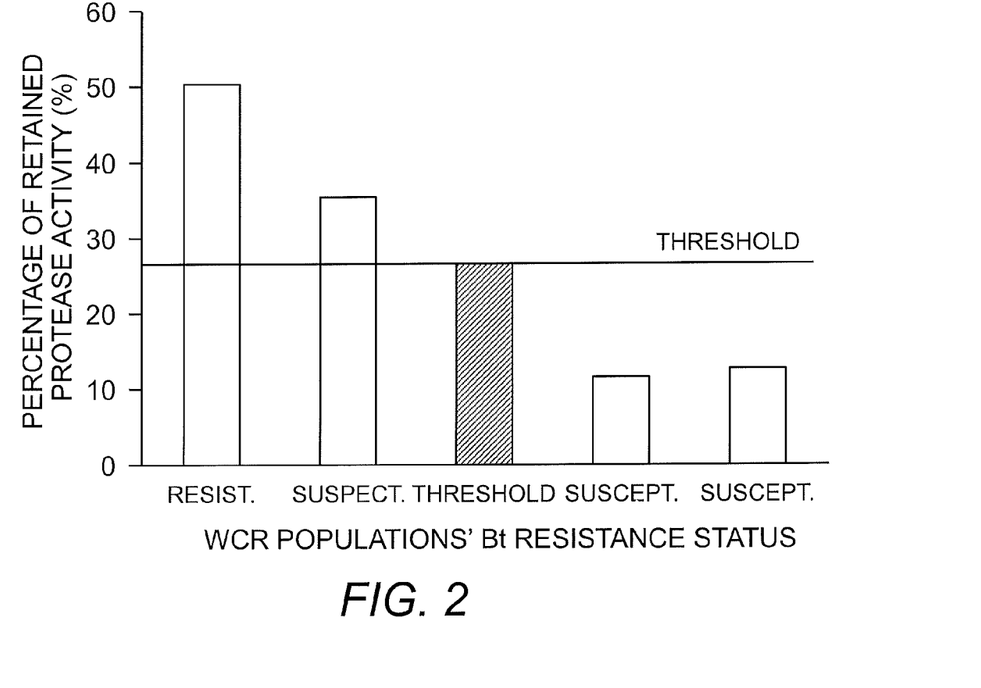
Figure 3A:
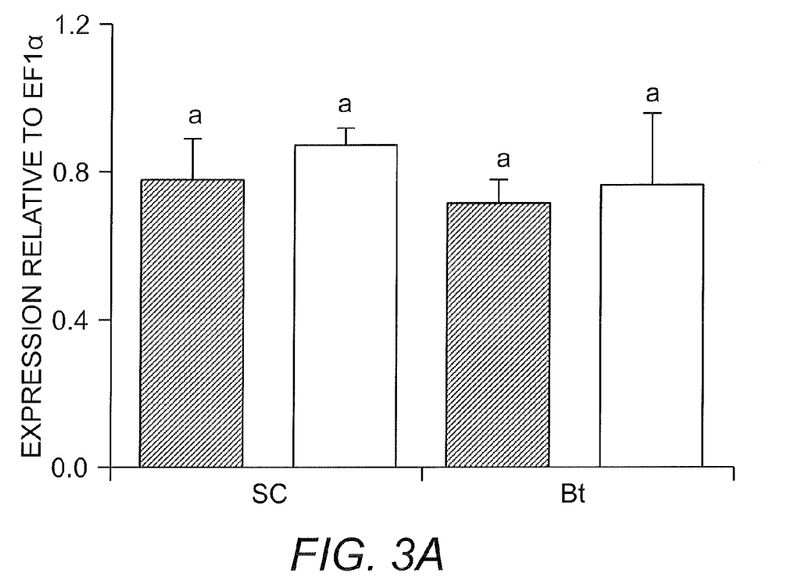
FIG. 3A shows cathepsin B1 (DvRS6) expression relative to Elongation Factor 1-α (EF-1α).
Figure 3B:
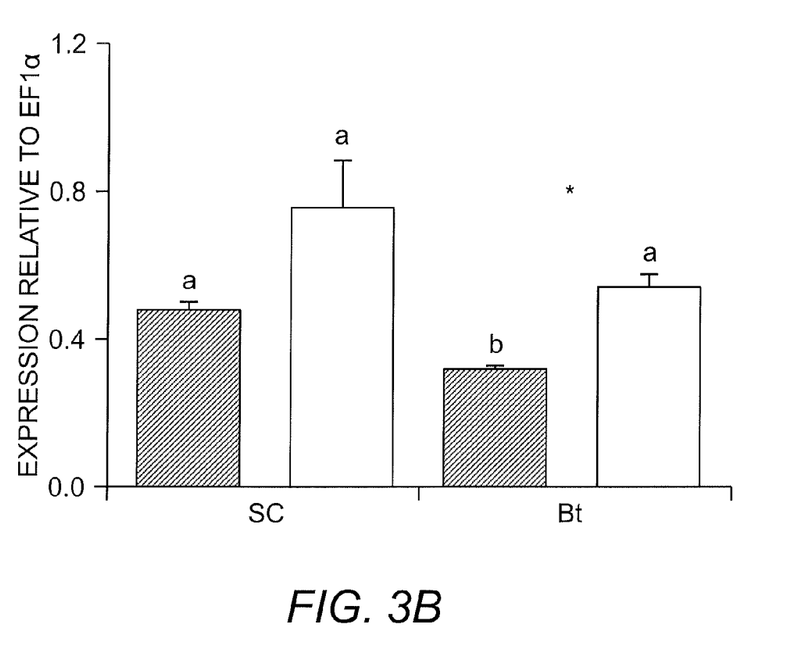
FIG. 3B shows cathepsin B2 (DvRS40) expression relative to EF-1α.
Figure 4A:
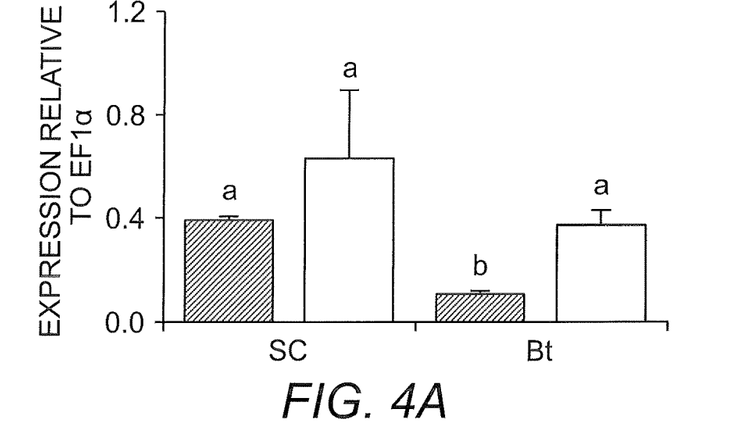
FIG. 4A shows cathepsin L1 (DvCAL1) expression relative to EF-1α.
Figure 4B:
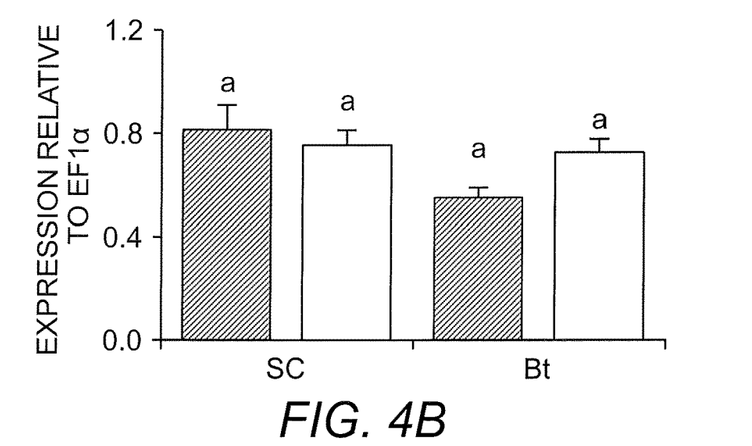
FIG. 4B shows cathepsin L2 (DvRS5) expression relative to EF1α.
Figure 4C:
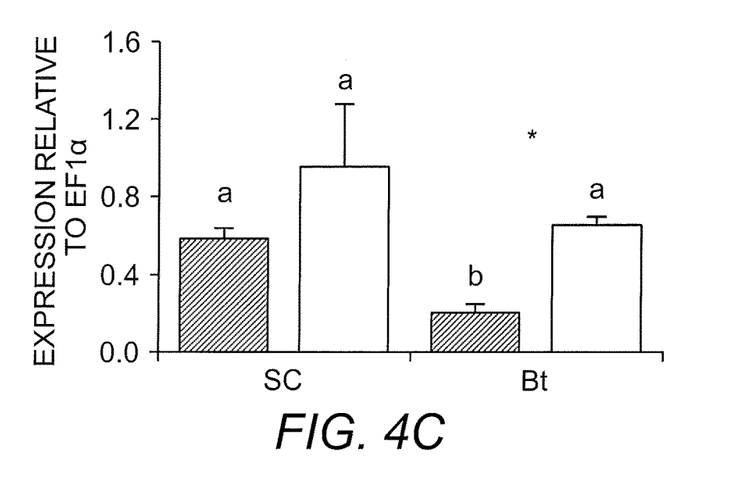
FIG. 4C shows cathepsin L3 (DvRS29) expression relative to EF1α.

In general, these results indicate that exposure to Bt toxin selected WCR individuals where the proteolytic activity of their guts was less affected by Bt, a sign of resistance. As such, the identity of resistant populations can be determined by comparing the level of protease activity in the gut of adult insects fed on a non-Bt and Bt diet, wherein insects with higher protease activity levels retained when fed on a Bt diet indicates that the population of insects has or is developing resistance to Bt (see FIG. 2).

In addition to activity, the expression of constitutive and inducible cysteine protease genes was also analyzed in response to Bt and non-Bt corn diets. In particular, WCR were fed a Bt or non-Bt corn diet and the level of expression of cathepsin L (L1, L2 and L3) and B genes (B1 and B2) was determined. This analysis indicated that after consumption of Bt toxin (Cry34/35), the level of specific cathepsin protease genes was significantly reduced in the susceptible population, but not the populations that were suspected to be in the process of resistance evolution (FIGS. 3A-3B and FIGS. 4A-4C). These results indicate that Bt toxins exert negative effects at the protease gene expression level, and that gene expression may be used in assays for determining resistance.

Overall, this analysis indicates that the gut physiology-based bioassay not only can provide information about evolution of resistance at the biochemical level but also at the nucleic acid level. In addition, the methods of the invention provide a relatively fast method to monitor resistance evolution in the field.

EXAMPLE 2

Bt Resistance Protease Activity Assay

Collection of Insects. Insect populations are collected from the field manually using nets or containers. A convenient method is to set up tents in non-Bt/Bt fields before adults emerge so that all insects emerging from the particular field are enclosed and available for sampling.

Insect Maintenance. All insects are kept on corn ears or silks from their original fields.

Dietary Treatments. Insects are treated with tissues of non-transgenic or transgenic corn tissues (with the trait to be tested). Insects are maintained on each diet for 5 (or 4) days.

Collection of Digestive Tract Samples. After dietary treatments, all insects are paralyzed with chloroform and complete digestive tracts are excised with fine tweezers. Multiple guts are pooled into one tube as an independent biological replicate (with the same sex ratio and gut number across treatments). For protease samples, four or more (depending on insect availability) guts are collected for one sample.

Extraction of Digestive Enzymes (i.e., Cysteine Proteases in WCR). Pooled gut samples are homogenized with micropestles in 30 mM Tri-K citrate (5 μl/mg gut tissue, pH 6.0) and placed on ice for 30 minutes. Samples are centrifuged for 15 minutes at 12,000 g and supernatants are collected into separate tubes. All samples are kept at −80° C. before measurements.

Digestive Enzyme Measurement. Supernatants (2 μl of protease samples) are added into 78 μl of reaction buffer (0.3 M KCl, 0.1 M $NaH_2PO_4$, 0.1 mM EDTA with 3 mM dithiothreitol, pH 6.0) containing 1 μM of cathepsin B inhibitor CA-074 [L-3-trans(propylcarbamyl) oxirane-2-carbonyl)-L-isoleucyl-L-proline]. Proteolysis reactions are started by adding the substrate, p-Glu-Phe-Leu-pNA, to a total concentration of 76 μM in each reaction. During the reaction, p-nitroaniline (pNA) released by substrate hydrolysis is monitored with a spectrophotometer at 405 nm.

Data Analysis. Different units of protease activity are calculated after the test (depending on the format needed). Absorbance units can be converted into nanomoles of pNA released based on calibration curves. The Bradford method (Bio-Rad) can also be used to determine protein concentrations in all gut protease samples and calculated into units of nmol pNA released per mg protein (or per mg gut tissue) per minute and compared across treatments. Depending on the distribution of the data, transformation could be preformed. Statistical comparison between treatments can be conducted using statistical software such as SPSS or SAS.

Interpretation of Data. After obtaining digestive enzyme activity results, decreases in digestive capacity after Bt toxin ingestion (Bt corn diet for example) are interpreted as fitness reduction of the gut system. Determination of resistance status can be determined based on whether the proportion of retained activity values of a tested WCR population exceeds that of a WCR population confirmed as a threshold population (pre-determined by, e.g., the seedling based assay). For each type of Bt toxin, multiple resistant populations can be tested and compared with susceptible insect populations.

The seedling-based assays can also be used with the same populations and the results can be compared between the two methods. In this respect, a threshold of fitness decrease can be set to determine toxin resistant using the method of this invention, which will enable direct testing of field insects and determining their resistance to the target toxin at high efficiency.

EXAMPLE 3

Bt Resistance Protease Gene Expression Assay

Collection of Insects. Insect populations are collected from the field manually using nets or containers. A convenient method is to set up tents in non-Bt/Bt fields before adults emerge so that all insects emerging from the particular field are enclosed and available for sampling.

Insect Maintenance. All insects are kept on corn ears or silks from their original fields.

Dietary Treatments. Insects are treated with tissues of non-transgenic or transgenic corn tissues (with the trait to be tested). Insects are maintained on each diet for 4 or 5 days (same across treatments).

Collection of Digestive Tract Samples. After dietary treatments, all insects are paralyzed with chloroform and complete digestive tracts are excised with fine tweezers. Multiple gut samples are pooled into one tube as an independent sample (with the same sex ratio and gut number across treatments). For RNA samples, five insect guts are pooled into one tube and 50 μl of RNALATER solution (Ambion) are added to prevent RNA degradation. All samples are kept at −80° C. before extraction. Biological replicates are used in all experiments.

RNA Extraction and Reverse-Transcription. RNALATER solution from collected gut samples is removed. Total RNA is extracted from gut tissue samples with an E.Z.N.A Total RNA Kit I (Omega Bio-Tek, Norcross, Ga.) according to the manufactures instructions, including the optional DNase treatments. Extracted RNA (250 ng) is reverse-transcribed into cDNA using the SUPERSCRIPT III First-Strand Synthesis System (Invitrogen) and oligo-dT primers.

Measuring Gene Expression. The reverse-transcribed cDNA products (10-fold) are diluted and subjected to Real-Time Quantitative RT-PCR (RQ-PCR, SYBR green method) analysis in an ABI PRISM 7900 HT Sequence Detection System (Applied Biosystems) using primers specific to the digestive enzyme genes. For internal controls, primers targeting suitable housekeeping genes can be used. For example, the WCR elongation factor-1 alpha gene (EF-1α) can be used as a control.

Interpretation of Data. After obtaining results from the gene expression profiles, decreases in gene expression levels (fold changes of gene expression) after toxin ingestion (Bt corn ear diets for example) are interpreted as fitness reduction of the gut system. For each toxin (Bt gene), multiple resistant populations can be tested and compared with susceptible insect populations. Determination of resistance status can be made based on whether the proportion of retained gene expression levels (of a protease gene) of a tested WCR population exceeds the proportion of a WCR population that has been confirmed to be a threshold population (pre-determined by, e.g., the seedling based assay).

What is claimed is:

1. A method of monitoring for resistance to a *Bacillus thuringiensis* pesticidal crystal protein comprising (a) collecting adult Coleopteran insects from a field of plants;

(b) feeding a first group of the adult Coleopteran insects a *Bacillus thuringiensis* pesticidal crystal protein (Bt) diet and feeding a second group of the adult Coleopteran insects a non-Bt diet;

(c) obtaining gut samples from the adult Coleopteran insects fed the Bt diet and non-Bt diet;

(d) measuring a level of protease activity or protease expression in the gut samples from the adult Coleopteran insects fed the Bt diet and non-Bt diet; and (e) determining resistance or susceptibility to the Bt pesticidal crystal protein by
  (i) averaging the level of protease activity or protease expression in the gut samples from the adult Coleopteran insects fed the Bt diet;
  (ii) averaging the level of protease activity or protease expression in the gut samples from the adult Coleopteran insects fed non-Bt diet;
  (iii) calculating a ratio of the average level of protease activity or protease expression in the gut samples from the adult Coleopteran insects fed the Bt diet to the average level of protease activity or protease expression in the gut samples from the adult Coleopteran insects fed non-Bt diet to obtain a retained level of protease activity or protease expression; and
  (iv) comparing the retained level of protease activity or protease expression with a threshold protease activity or expression standard, wherein resistance to the pesticidal crystal protein is indicated if the retained level of protease activity or protease expression exceeds the threshold protease activity or expression standard.

2. The method of claim 1, wherein the threshold protease activity or expression standard is a mean of
  (i) an average retained protease activity or protease expression of resistant populations of adult Coleopteran insects, and
  (ii) an average retained protease activity or protease expression of susceptible populations of adult Coleopteran insects.

3. The method of claim 1, wherein the threshold protease activity or expression standard is a retained activity or expression level of a Coleopteran insect population that is in the process of developing resistance to a *Bacillus thuringiensis* pesticidal crystal protein.

\* \* \* \* \*